(12) United States Patent
Wakasugi et al.

(10) Patent No.: US 8,147,474 B2
(45) Date of Patent: Apr. 3, 2012

(54) ABSORBENT ARTICLE

(75) Inventors: Kei Wakasugi, Kagawa (JP); Hirotomo Mukai, Kagawa (JP); Tomoko Tsuji, Kagawa (JP); Kenichi Sasayama, Kagawa (JP); Tatsuya Hashimoto, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 490 days.

(21) Appl. No.: 11/945,404

(22) Filed: Nov. 27, 2007

(65) Prior Publication Data

US 2008/0125740 A1    May 29, 2008

(30) Foreign Application Priority Data

Nov. 27, 2006   (JP) .................................. 2006-319392

(51) Int. Cl.
*A61F 13/15* (2006.01)

(52) U.S. Cl. ............ 604/385.22; 604/385.31; 604/385.3

(58) Field of Classification Search ............. 604/385.22, 604/385.26, 385.29, 385.3, 385.31
See application file for complete search history.

(56) References Cited

U.S. PATENT DOCUMENTS

| | | | | |
|---|---|---|---|---|
| 4,710,189 A | * | 12/1987 | Lash | 604/385.27 |
| 4,891,258 A | * | 1/1990 | Fahrenkrug | 428/138 |
| 5,389,095 A | * | 2/1995 | Suzuki et al. | 604/385.22 |
| 5,451,219 A | * | 9/1995 | Suzuki et al. | 604/385.22 |
| 5,576,090 A | * | 11/1996 | Suzuki | 428/152 |
| 2002/0193774 A1 | * | 12/2002 | Otsubo | 604/385.22 |
| 2004/0243086 A1 | * | 12/2004 | VanGompel et al. | 604/385.3 |

FOREIGN PATENT DOCUMENTS

| | | |
|---|---|---|
| JP | 06-090979 | 4/1994 |
| JP | 10-245757 A1 | 9/1998 |
| JP | 2002-143218 | 5/2002 |
| JP | 2004-136068 | 5/2004 |
| JP | 2005-052225 | 3/2005 |
| JP | 2007-300940 | 11/2007 |

* cited by examiner

*Primary Examiner* — Lynne Anderson
(74) *Attorney, Agent, or Firm* — Morrison & Foerster LLP

(57) ABSTRACT

The present invention provides an absorbent article 1 that does not easily warp in a leg-surrounding portion. The absorbent article 1 includes an absorbing member 2 in an elongated shape arranged along a longitudinal direction of the absorbent article, and a stretchable chassis 3 having a leg-surrounding portion 3a recessed inward in a width direction. At least a part of the chassis 3 is composed of a composite sheet 13 obtained by affixing a stretchable sheet 15 and a non-stretchable sheet 16 to each other by a plurality of adhesive portions 18. The leg-surrounding portion 3a has an intersection crossing an expansion and contraction direction of the chassis 3 at a predetermined angle. The plurality of adhesive portions 18 extend in a direction substantially perpendicular to the expansion and contraction direction.

8 Claims, 7 Drawing Sheets

ABSORBENT ARTICLE

This application is based on and claims the benefit of priority from Japanese Patent Application No. 2006-319392, filed on Nov. 27, 2006, the content of which is incorporated herein by reference.

BACKGROUND OF THE INVENTION

1. Field of the Invention

The present invention relates to an absorbent article including a composite sheet obtained by affixing two types of sheets having different ratios of expansion and contraction.

2. Related Art

Conventionally, disposable diapers, for example, have been known as absorbent articles. The disposable diapers widely employed for babies and children to the elderly persons and physically-handicapped persons have been replaced with reusable absorbent articles made of cloth. Such a disposable diaper generally includes an absorbing member in an elongated shape arranged along a longitudinal direction and a chassis having a leg-surrounding portion recessed inward in a width direction on both sides in the width direction formed therein, and composed of a composite sheet obtained by affixing two sheets. According to Japanese Unexamined Patent Application, First Publication No. 2004-136068 (hereinafter referred to as "patent publication 1"), some composite sheets have been manufactured by a method of coating the whole surface of one of the two sheets with adhesives, finely arranging a thread-shaped stretchable member between the two sheets, and bonding the other sheet thereto.

Figure 6:
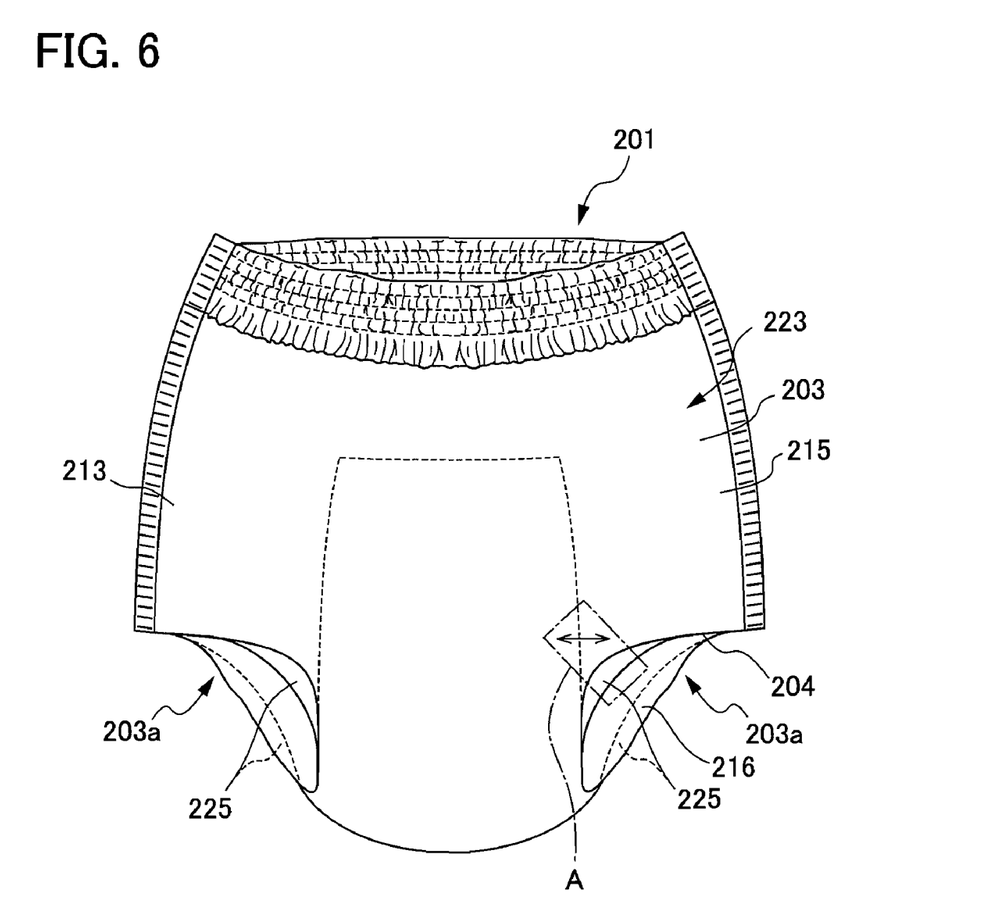
FIG. 6 is an exploded view of a conventional disposable diaper.

Additionally, as disclosed in Japanese Unexamined Patent Application, First Publication No. 2002-143218 (hereinafter referred to as "patent publication 2"), there is also a technique for affixing a sheet-shaped stretchable sheet to a non-stretchable sheet to manufacture a composite sheet in order to enhance the appearance and the fitting properties of a diaper in the shape of pants. FIG. 6 is a front view of a diaper in the shape of pants 201 using a composite sheet 213 obtained by affixing such stretchable and non-stretchable sheets 215 and 216, respectively, to each other for portions including a trunk-surrounding portion and a leg-surrounding portion of the diaper. The composite sheet 213 is formed of two sheets, i.e., the non-stretchable sheet 216 on the side of a skin contacting surface directed toward the body of a wearer and the stretchable sheet 215 on the side of a non-skin contacting surface that is the opposite side of the skin contacting surface and affixed to each other with adhesives applied to the entire surfaces of the sheets.

Figure 7:
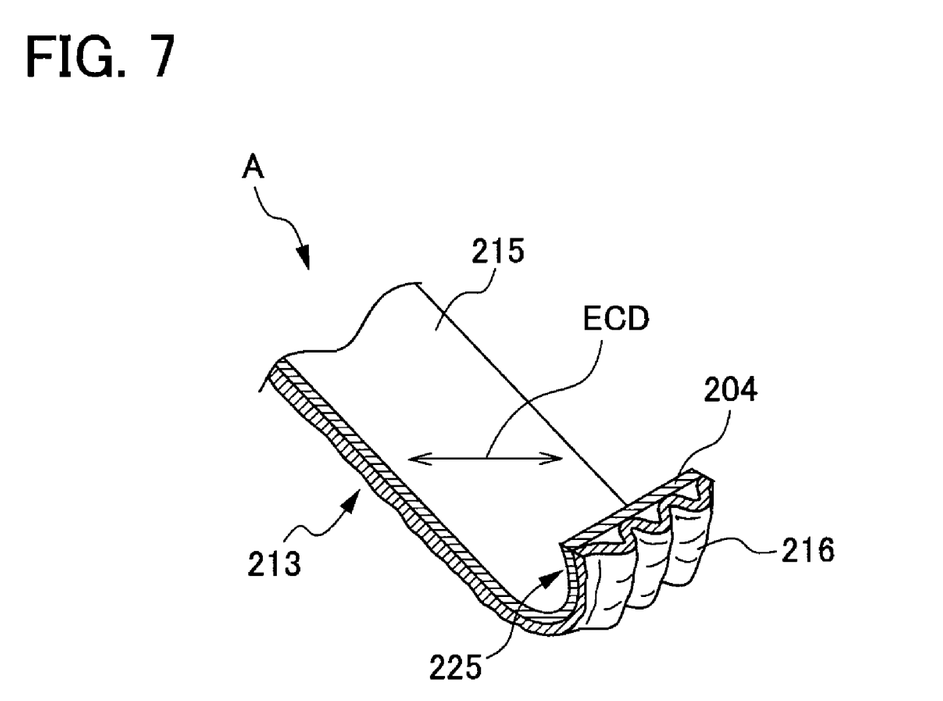
FIG. 7 is an enlarged view of the region A of FIG. 6, showing a warping portion occurring at a cut edge of the conventional disposable diaper.

When the non-stretchable sheet 216 and the stretchable sheet 215 are thus affixed to each other with the adhesives applied to the entire surfaces of the sheets, a warping portion 225 that warps toward the non-skin contacting surface, i.e., a portion having a height no less than two times that of the other portions in a stationary state or a portion with a front surface appearing to be turned toward the reverse surface or reverse surface appearing to be turned toward the front surface in a stationary state occurs at a cut edge 204 of a leg-surrounding portion 203a. FIG. 7 is an enlarged view of the region A of FIG. 6, showing a cross-sectional view of a portion where such a warping portion 225 occurs. The arrows show an expansion and contraction direction (ECD) at the portion. The non-stretchable sheet 216 on the side of the skin contacting surface is pulled with a contractive force of the stretchable sheet 215 on the side of the non-skin contacting surface so that the warping portion 225 occurs. When the warping portion 225 is thus provided in the chassis 203, adhesion between the skin and the composite sheet 213 is degraded, so that a gap occurs between the skin and the composite sheet 213. Therefore, urine is likely to leak out of the gap.

An objective of the present invention is to provide an absorbent article that does not easily warp in a leg-surrounding portion.

The inventors of the present invention have performed thorough examination in order to attain the above-mentioned objective. As a result, they have found that when a stretchable sheet and a non-stretchable sheet are bonded to each other, and adhesive portions are provided to extend in a direction substantially perpendicular to an expansion and contraction direction between the sheets at a cut edge of both the sheets to prevent a warping portion from occurring at the cut edge, the present invention is achieved. Specifically, an objective is to provide the absorbent article described below.

SUMMARY OF THE INVENTION

In a first aspect of the present invention, an absorbent article has a width direction and a longitudinal direction perpendicular to the width direction, and includes an absorbing member in an elongated shape disposed along an longitudinal direction of the absorbent article; and a stretchable chassis having a leg-surrounding portion recessed inward in a width direction of the absorbent article on both sides in the width direction formed therein, in which at least a portion of the chassis is composed of a stretchable composite sheet obtained by affixing, by way of a plurality of adhesive portions, a first sheet and a second sheet having a ratio of expansion and contraction that is different from that of the first sheet, the leg-surrounding portion having an intersection crossing an expansion and contraction direction of the chassis at a predetermined angle, and the plurality of adhesive portions extend with predetermined spacing in the expansion and contraction direction at the intersection and in a direction substantially perpendicular to the expansion and contraction direction.

In a second aspect of the absorbent article as described in the first aspect of the present invention, the predetermined angle is in the range of 20 degrees to 90 degrees.

In a third aspect of the absorbent article described in the first or second aspect of the present invention, the difference in ratios of expansion and contraction in the composite sheet between the first sheet and the second sheet, respectively, is at least 20%.

In a fourth aspect of the absorbent article as described in any one of the first to third aspects of the present invention, a size in the expansion and contraction direction of the plurality of adhesive portions is in the range of 0.1 mm to 20 mm.

In a fifth aspect of the absorbent article as described in any one of the first to fourth aspects of the present invention, among the plurality of adhesive portions, the spacing between the adhesive portions adjacent to each other at the intersection of the leg-surrounding portion is in the range of 4 mm to 25 mm.

In a sixth aspect of the absorbent article as described in any one of the first to fifth aspects of the present invention, the expansion and contraction direction is the width direction, and each of the plurality of adhesive portions is formed in a linear shape extending in a direction substantially perpendicular to the expansion and contraction direction.

In a seventh aspect of the absorbent article as described in any one of the first to sixth aspects of the present invention, the ratio of the dimensions of the plurality of adhesive portions in the vicinity of the intersection is in the range of 0.4% to 83%.

In an eighth aspect of the absorbent article as described in any one of the first to seventh aspects of the present invention, the adsorbent article is a diaper in the shape of pants.

The present invention provides an absorbent article that does not easily warp in a leg-surrounding portion.

DETAILED DESCRIPTION OF THE INVENTION

First Embodiment

A disposable diaper 1 serving as an absorbent article according to a first embodiment of the present invention is now described while referring to the drawings. In the following description, a surface directed toward the body of a wearer of the disposable diaper is considered as a skin contacting surface, and a surface on the opposite side of the skin contacting surface is considered as a non-skin contacting surface.

Figure 1:
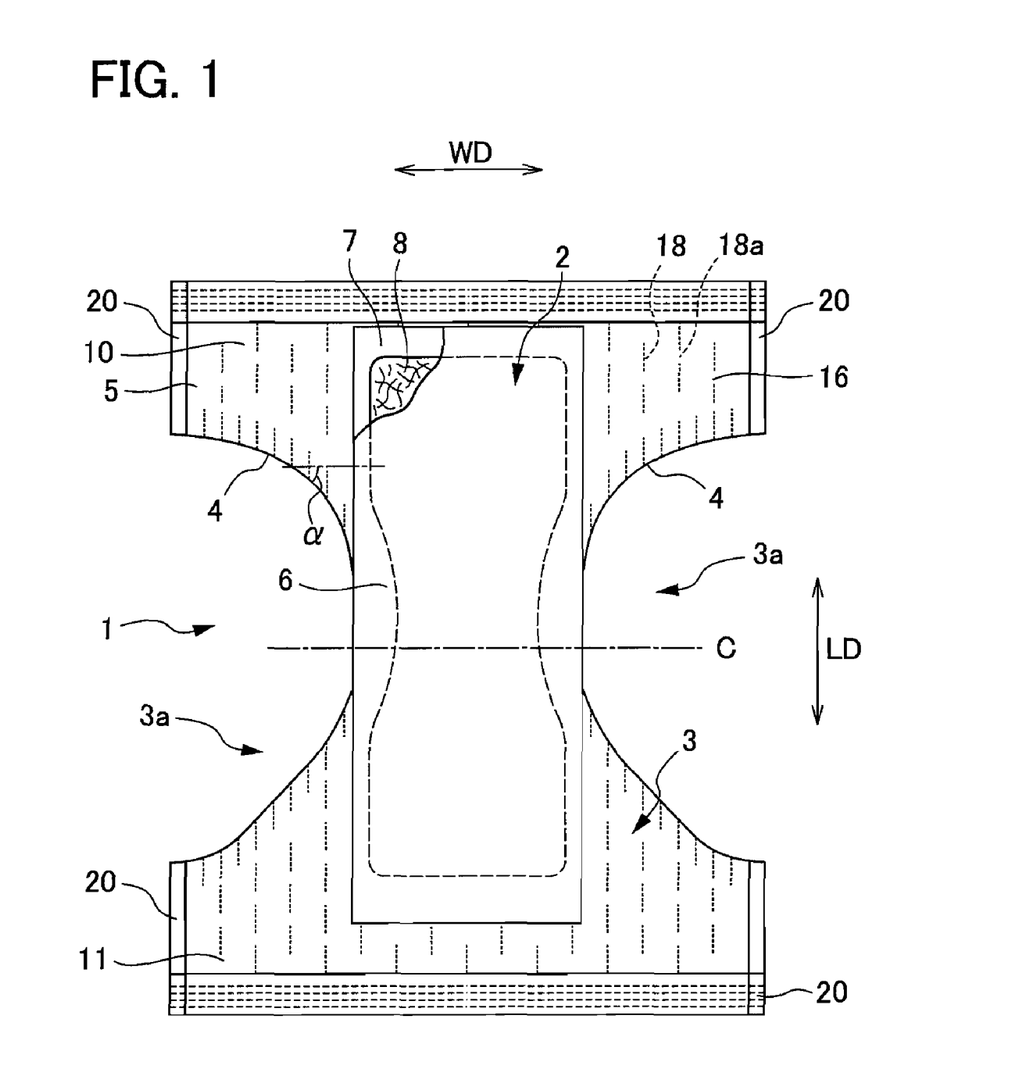
FIG. 1 is an exploded view of a disposable diaper according to a first embodiment of the present invention.
Figure 2:
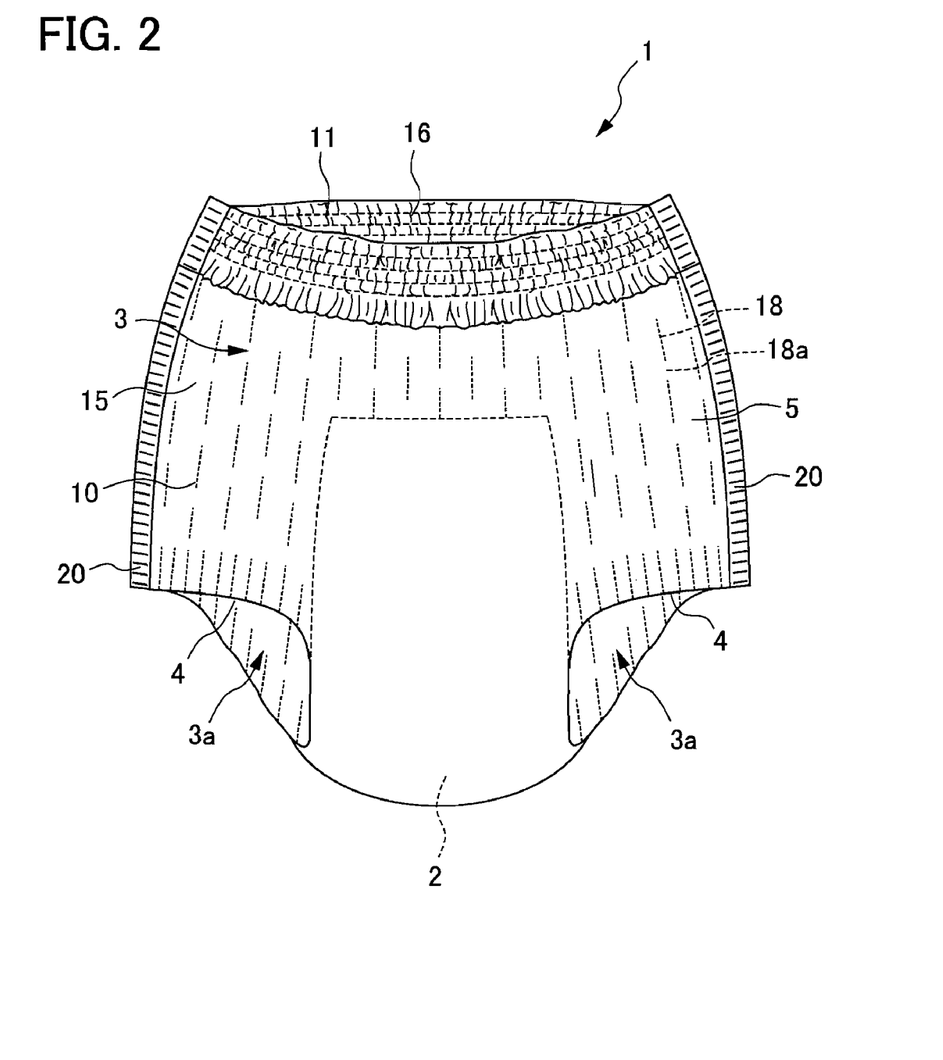
FIG. 2 is a front view of the disposable diaper, formed in the shape of pants, according to the first embodiment of the present invention.

FIG. 1 is an exploded view of the disposable diaper 1 according to the first embodiment. FIG. 2 is a front view of the disposable diaper 1, formed in the shape of pants shown in an unfolded state in FIG. 1. As shown in FIG. 1, the disposable diaper 1 includes an absorbing member 2 in an elongated shape arranged along a longitudinal direction (LD) and a stretchable chassis 3 having a leg-surrounding portion 3a recessed in a U-shape inward on both sides in a width direction (WD) formed therein.

First, the chassis 3 is described. As shown in FIG. 1, the chassis 3 has the U-shaped leg-surrounding portion 3a recessed inward in the width direction on both sides in the width direction formed therein, as described above. The chassis 3 is divided into two portions, i.e., a front body portion 10 and a rear body portion 11, by a line C passing through a portion, which becomes the narrowest by U-shaped cuts of the leg-surrounding portion 3a of the chassis 3 and extending in the width direction. If we let $\alpha$ be an angle of a cut edge 4 of the leg-surrounding portion 3a to an expansion and contraction direction of the chassis 3 (the width direction) at the cut edge 4, as illustrated, at an end in the width direction of the front body portion 10, the angle $\alpha$ is 0 degrees, that is, the cut edge 4 is parallel to the expansion and contraction direction of the chassis 3. The angle $\alpha$ gradually increases from the position of the end toward the center in the width direction of the chassis 3 to a position where the chassis 3 and the absorbing member 2 overlap with each other, to form an intersection crossing the expansion and contraction direction of the chassis 3. At the position where the chassis 3 and the absorbing member 2 overlap with each other, the angle $\alpha$ is approximately 90 degrees.

Figure 3:
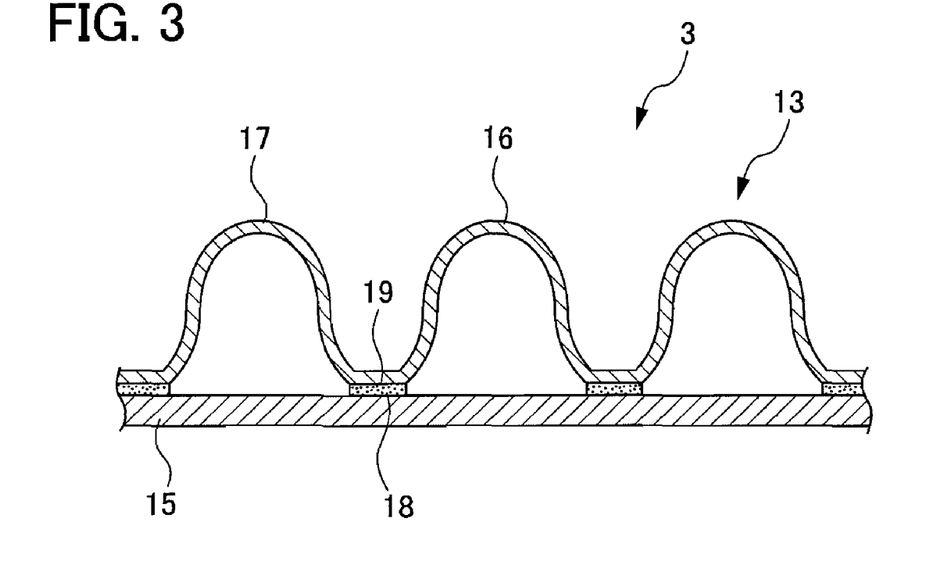
FIG. 3 is a cross-sectional view showing a state where a stretchable sheet and a non-stretchable sheet are affixed to each other.

FIG. 3 is a cross-sectional view of the chassis 3 from the width direction. A sheet composing the chassis 3 is a composite sheet 13 obtained by affixing a stretchable sheet 15 and a non-stretchable sheet 16 to each other in adhesive portions 18 with an adhesive 19 such as a hot melt adhesive, as illustrated. This composite sheet 13, produced by affixing the stretchable sheet 15 in its expanded state to the non-stretchable sheet 16, can expand and contract in the width direction and is placed on the chassis 3 so as to expand and contract in the width direction. With the stretchable sheet 15 relaxed, a plurality of pleats 17 are formed in a direction perpendicular to the expansion and contraction direction in non-adhesive portions, which are not joined to the stretchable sheet 15, of the non-stretchable sheet 16.

A material for the stretchable sheet 15 can be changed as required, in accordance with the intended use or the like of the absorbent article. For example, various types of known stretchable sheets 15 such as a spunbonded sheet and a meltblown sheet can be selected. Usable as fibers constituting the stretchable sheets 15 are polyolefin-, polyester-, or polyamide-based fibers, or core-sheath type conjugate fibers or side-by-side type conjugate fibers formed of polyethylene/polypropylene or polyethylene/polyester. Furthermore, a stretchable sheet 15 obtained by melting and spinning urethane-based thermoplastic synthetic resin to produce a spunbonded sheet and stretching the spunbonded sheet in at least one direction to develop stretchable elasticity may be used.

Although the basis weight of the stretchable sheet 15 can be changed as required, in accordance with the intended use or the like, it is preferably 20 to 80 g/m$^2$ before the stretchable sheet 5 is affixed to the non-stretchable sheet 16. When the basis weight of the stretchable sheet 15 is less than 20 g/m$^2$, the strength thereof may, in some cases, decrease. On the other hand, when the basis weight of the stretchable sheet 15 exceeds 80 g/m$^2$, the thickness thereof may, in some cases, increase.

The strength at the time of 100 percent expansion of the stretchable sheet 15 is preferably not more than 10 N/50 mm and more preferably in the range of 1 to 7 N/50 mm.

Furthermore, the strain of the stretchable sheet 15 after 100 percent expansion is preferably not more than 15%, and more preferably not more than 10%.

A material for the non-stretchable sheet 16 can be changed as required, in accordance with the intended use or the like of the absorbent article. For example, various types of known non-stretchable sheets 16 such as a spunbonded sheet, an SMS (spunbond/meltblown/spunbond) sheet, a point-bonded sheet, a through-air sheet, a spun lace sheet, and a needle punch sheet can be selected. They may be used alone or in combination. Usable as fibers composing the non-stretchable sheets 16 are polypropylene-, polyolefin-, polyester-, or polyamide-based fibers, or core-sheath type conjugate fibers or side-by-side type conjugate fibers formed of polyethylene/polypropylene or polyethylene/polyester.

Although the basis weight of the non-stretchable sheet 16 can be changed as required, in accordance with the intended use or the like, it is preferably in the range of 10 to 50 g/m$^2$. When the basis weight of the stretchable sheet 16 is less than 10 g/m$^2$, the strength thereof may in some cases decrease. On the other hand, when the basis weight of the non-stretchable sheet 16 exceeds 50 g/m$^2$, the thickness thereof may in some cases increase. When the thickness of the non-stretchable sheet 16 increases, the rigidity thereof increases, thereby inhibiting the stretchability. This causes the flexibility of the composite sheet 13 to be reduced.

Examples of a coating method of adhesives for bonding the stretchable sheet 15 and the non-stretchable sheet 16 to each other include control seam coating, coater coating, curtain coater coating, and summit gun coating. The basis weight of adhesives in hot melt adhesion is preferably in the range of 1 to 30 g/m$^2$ and more preferably in the range of 3 to 10 g/m$^2$.

The absorbing member 2 is next described. The absorbing member 2 has a liquid-permeable top sheet 6 in a substantially longitudinal shape composing a front surface layer, a liquid-impermeable back sheet 7 in a substantially vertically-long shape constituting a reverse surface layer, and an absorbent body 8 in a substantially rectangular shape having liquid holding properties and constituting an absorbing layer arranged between the liquid-permeable top sheet 6 and the liquid-impermeable back sheet 7. The absorbing member 2 is affixed to a surface, on the side of the skin contacting surface, at the center of the chassis 3 such that the liquid-impermeable back sheet 7 and the chassis 3 are opposed to each other.

It should be noted that "substantially longitudinal shape" indicates a substantially rectangular or elliptical shape having a longer-side direction (longitudinal direction) and a shorter-side direction, and further includes such a shape in which parts of both the sides in the longitudinal direction are recessed in a direction toward the center in the longitudinal direction or projected in the opposite direction to the direction toward the center. More specifically, the absorbent body 8 in a substantially longitudinal shape includes one having portions that differ in width along the longitudinal direction. Although the absorbent body 8 extends in the longitudinal direction in the present embodiment, the present invention is not limited to the same. The absorbent body 8 may extend in the width direction.

Furthermore, the absorbent body 8 may be arranged in a state in which it is wrapped in a tissue (not shown) or a hydrophilic sheet (not shown). When wrapped in the hydrophilic sheet, the absorbent body 8 may not use the liquid-permeable top sheet 6 or may only partially use the liquid-permeable top sheet 6. This allows the production cost to be reduced, for example. Furthermore, a sheet such as a nonwoven fabric may be joined to a surface on the side of the non-skin contacting surface of the liquid-impermeable back sheet 7, which is preferable because the feel against the skin of a wearer at the time of wearing, for example, is improved. Alternatively, when a film is used for the liquid-impermeable back sheet 7, a sheet or the like may be joined to the film, which is preferable because an undesired sound can be prevented from being produced by friction of the film, for example.

The absorbent body 8 is for absorbing and holding a discharged body fluid such as urine, and may be formed by mixing and laminating a highly absorbent polymer and hydrophilic fibers, or formed by fixing a highly absorbent polymer to a hydrophilic sheet with a hot melt adhesive or the like.

The liquid-permeable top sheet 6 is arranged on the side of the body and is brought into contact with an excretory portion when it is employed. Examples of the liquid-permeable top sheet 6 include not only one having an entire surface liquid-permeable, but also one that is partially liquid-permeable. Furthermore, the liquid-permeable top sheet 6 may be composed of one sheet-shaped member or may be formed by bonding a plurality of sheet-shaped members to one another.

Preferable as the liquid-permeable top sheet 6 is a material that has enough strength so as not to be damaged, even if a load is applied thereto due to compression, torsion, friction or the like during wearing, and does not irritate the skin. Usable as the material is a sheet-shaped material having liquid permeability such as a woven fabric, a nonwoven fabric, or a porous plastic sheet.

Although the liquid-impermeable back sheet 7 is arranged on the side of the non-skin contacting surface so as to be opposed to the chassis 3, as described above, the present invention is not limited to the same. For example, it may be provided among a plurality of sheets constituting the chassis 3.

A coating pattern of the adhesive portions 18 in the chassis 3 is described next. As indicated by dotted lines in FIGS. 1 and 2, in a trunk-surrounding portion 5 in the chassis 3, the adhesive portions 18 inconsistently extend, respectively, with predetermined lengths along a plurality of straight lines extending with predetermined spacing in the longitudinal direction. The adhesive portions 18 on the adjacent straight lines are alternate. That is, the adhesive portions 18 extend in a direction substantially perpendicular to the expansion and contraction direction of the chassis 3. A cut portion 18a of the adhesive portion 18 on the one straight line is not present at the same position in the longitudinal direction as a cut portion 18a of the adhesive portion 18 on the adjacent straight line. It should be noted that the size (width) in the expansion and contraction direction of the adhesive portions 18 is preferably in the range of 0.1 mm to 20 mm, and is 2.5 mm in the present embodiment.

Furthermore, at the cut edge 4 of the leg-surrounding portion 3a, the adhesive portions 18 extend in the longitudinal direction, similarly to those in the trunk-surrounding portion 5. That is, the adhesive portions 18 extend in a direction substantially perpendicular to the expansion and contraction direction of the chassis 3 in all regions of the leg-surrounding portion 3a, irrespective of an angle of the cut edge 4 to the expansion and contraction direction of the chassis 3. In this embodiment, the spacing in the width direction of the adhesive portions 18 at the cut edge 4 of the leg-surrounding portion 3a is denser than that in the trunk-surrounding portion 5, and is approximately one-half that in the trunk-surrounding portion 5. Specifically, the spacing between the adhesive portions 18 in the leg-surrounding portion 3a is preferably at least 4 mm. If the spacing between the adhesive portions 18 is too great, however, a space is noticeable at an end of the leg-surrounding portion 3a. Therefore, the spacing is appropriately not more than 25 mm, although it varies depending on a ratio of expansion and contraction. Therefore, by making the spacing between the adhesive portions 18 at the cut edge 4 of the leg-surrounding portion 3a narrower than that in the trunk-surrounding portion 5, integration between the stretchable sheet 15 and the non-stretchable sheet 16 in the composite sheet 13 is improved to improve fitting properties to the body, which can inhibit urine leakage or the like. The minimum area ratio of the adhesive portions 18 to the composite sheet 13 in the vicinity of an intersection at which the cut edge 4 crosses the expansion and contraction direction of the chassis 3 is $0.1/(0.1+24) \times 100 = 0.4\%$, because the width of the adhesive portions 18 is in the range of 0.1 mm to 20 mm and the spacing between the adjacent adhesive portions 18 is in the range of 4 mm to 25 mm. On the other hand, the maximum area ratio is $20/(20+4) \times 100 = 83\%$. Consequently, the area ratio is preferably in a range of 0.4% to 83%. Here, "vicinity" indicates a predetermined region between the cut edge 4 and a curve separated from the cut edge 4 by a length that is not more than the respective lengths of the adhesive portions 18.

The disposable diaper 1 having the above-mentioned configuration is folded from the unfolded state shown in FIG. 1, and is formed in the shape of pants as shown in FIG. 2 by intermittently joining the front body portion 10 and the rear body portion 11 at joining portions 20 provided on both sides in the width direction using ultrasonic sealing, heat sealing, or the like.

The disposable diaper 1 formed in the shape of pants is generally in the state shown in FIG. 3, where the stretchable sheet 15 does not expand so that the plurality of pleats 17 are formed in the non-stretchable sheet 16. When the chassis 3 is extended in the width direction at the time of wearing, for example, the stretchable sheet 15 expands so that the pleats in the non-stretchable sheet 16 become smooth.

As described above, according to the present embodiment, the adhesive portions 18 extend in the direction substantially perpendicular to the expansion and contraction direction of the chassis 3 in all of the regions of the leg-surrounding portion 3a, i.e., the intersection at which the cut edge 4 of the leg-surrounding portion 3a crosses the expansion and contraction direction of the chassis 3 at a large angle. Therefore, even if at the cut edge 4 of the leg-surrounding portion 3a, the stretchable sheet 15 on the side of the non-skin contacting surface contracts, the non-stretchable sheet 16 on the side of the skin contacting surface is pulled toward the stretchable sheet 15 due to the presence of the adhesive portions 18, thereby inhibiting the disposable diaper 1 from warping outward. The warping is thus inhibited, which prevents urine leakage or the like.

Second Embodiment

Figure 4:
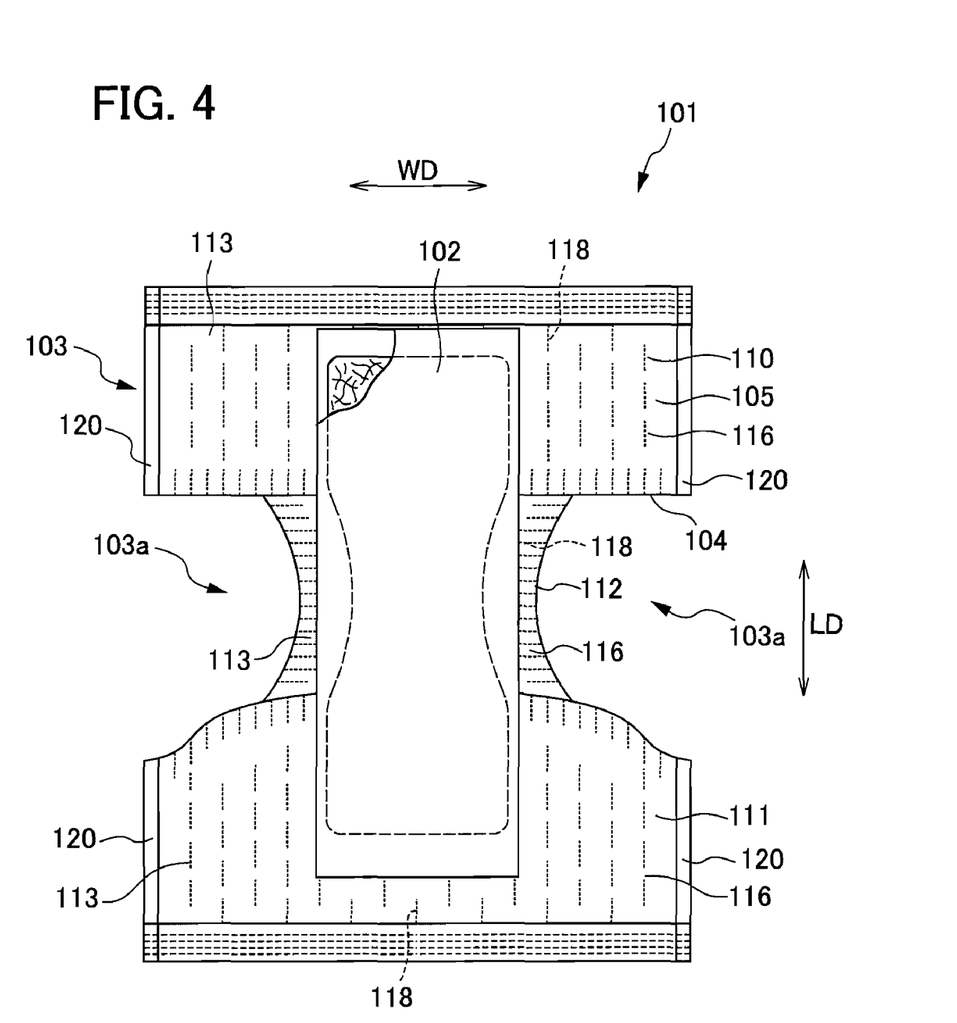
FIG. 4 is an exploded view of a disposable diaper according to a second embodiment of the present invention.

A disposable diaper 101 serving as an absorbent article according to a second embodiment of the present invention is now described while referring to the drawings. In the second embodiment, the same descriptions as those in the first embodiment are not repeated. FIG. 4 is an exploded view of the disposable diaper 101 according to the second embodiment. The present embodiment differs from the first embodiment in that a chassis 103 is not formed as an integral member and, in addition to a front body portion 110 and a rear body portion 111 that expand and contract in a width direction (WD), has an intermediate body portion 112 that is arranged between the front body portion 110 and the rear body portion 111, which expands and contracts in a longitudinal direction (LD).

The front body portion 110 is a substantially rectangular member in a horizontally-long shape extending in the width direction. The front body portion 110 is composed of a composite sheet 113 including a stretchable sheet (not shown in FIG. 4) and a non-stretchable sheet 116, and expands and contracts in the width direction, as in the first embodiment.

Although the rear body portion 111 is also a substantially rectangular member in a horizontally-long shape extending in the width direction, it is slightly curved in order to fit the body better at a cut edge 104 of a leg-surrounding portion 103a. The rear body portion 111 is composed of a composite sheet 113 including a stretchable sheet and a non-stretchable sheet 116, and expands and contracts in the width direction, similarly to the front body portion 110.

The intermediate body portion 112 positioned between the front body portion 110 and the rear body portion 111 is a substantially longitudinal member extending in the longitudinal direction. The cut edge 104 is curved in a U shape so as to be smoothly continuous from respective cut edges of the front body portion 110, the intermediate body portion 112, and the rear body portion 111. Although the intermediate body portion 112 is composed of a composite sheet 113 including a stretchable sheet and a non-stretchable sheet 116, similarly to the front body portion 110, it expands and contracts in the longitudinal direction.

An absorbing member 102 formed in the same manner as that in the first embodiment is made to adhere over a range from the front body portion 110 to the rear body portion 111 centered at the intermediate body portion 112.

Figure 5:
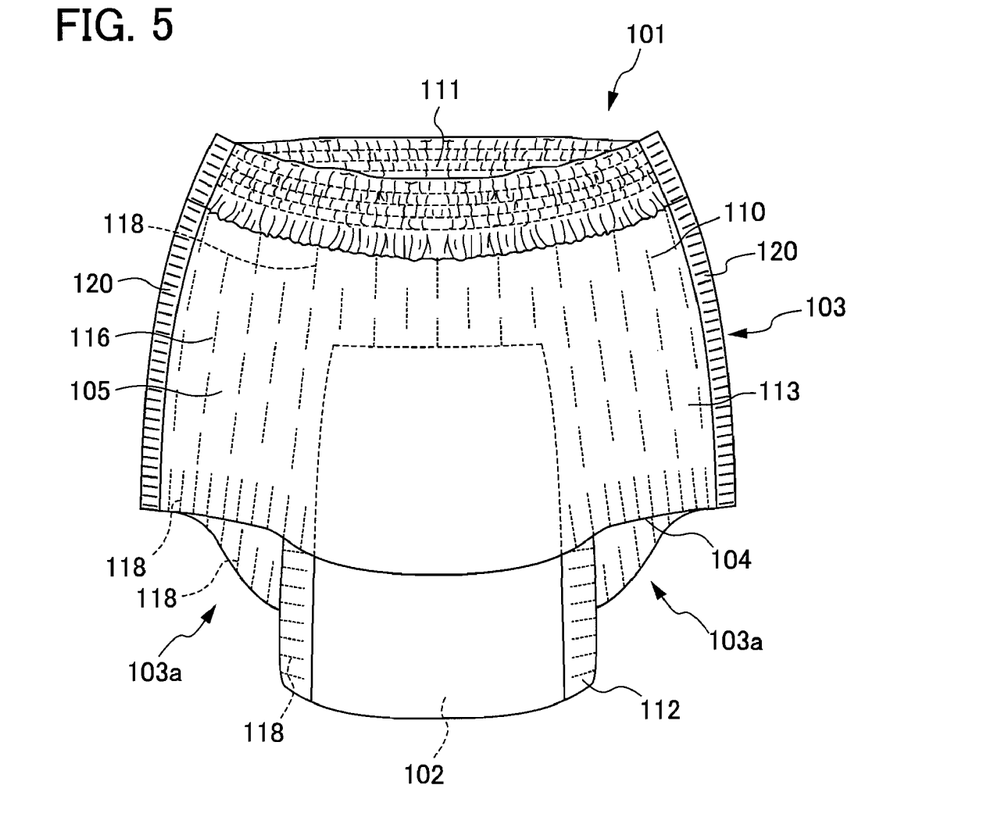
FIG. 5 is a front view of the disposable diaper, formed in the shape of pants, according to the second embodiment of the present invention.

The chassis 103 composed of the composite sheet 113 and in an unfolded state, as shown in FIG. 4, where the absorbing member 102 affixed to its center is folded, is formed in the shape of pants, as shown in FIG. 5, by intermittently joining the front body portion 110 and the rear body portion 111, respectively, to joining portions 120 provided on both sides in the width direction using ultrasonic sealing, heat sealing, or the like, as in the first embodiment.

A coating pattern of adhesive portions 118 in the front body portion 110 and the rear body portion 111 that expand and contract in the width direction are described. As indicated by dotted lines in FIGS. 4 and 5, the adhesive portions 118 intermittently extend, respectively, with predetermined lengths along a plurality of straight lines extending with predetermined spacing in the longitudinal direction, as in the first embodiment. The adhesive portions 118 on the adjacent straight lines extend so as to alternate. That is, the adhesive portions 118 extend in a direction substantially perpendicular to an expansion and contraction direction of the chassis 103.

In the leg-surrounding portion 103a in the front body portion 110 and the rear body portion 111, the direction in which the adhesive portions 118 extend is the longitudinal direction, as in the other portions, i.e., the direction substantially perpendicular to the expansion and contraction direction of the chassis 103. In this embodiment, the spacing in the width direction between the adhesive portions 118 in the leg-surrounding portion 103a is approximately one-half that in the width direction in a trunk-surrounding portion 105.

As stated above, the present embodiment is a case in which the expansion and contraction direction of the chassis and that of the intermediate body portion 112, the front body portion 110, and the rear body portion 111 are different. In this respect, the adhesive portions 118 in the intermediate body portion 112 extend in a direction parallel to the expansion and contraction direction of the chassis 103 (width direction), and are applied along a plurality of straight lines arranged with predetermined spacing in the longitudinal direction. In this manner, although an expansion and contraction direction of the intermediate body portion 112 differs from that of the front body portion 110 and the rear body portion 111, the adhesive portions 118 extend in a direction substantially perpendicular to the expansion and contraction direction in the leg-surrounding portion 103a.

As described above, according to the present embodiment, the adhesive portions 118 extend in a direction substantially perpendicular to the expansion and contraction direction of the chassis 103 in all regions of the leg-surrounding portion 103a. That is, the adhesive portions 118 extend so as to be substantially perpendicular to the expansion and contraction direction of the front body portion 110 and the rear body portion 111, and so as to be substantially perpendicular to the expansion and contraction direction of the intermediate body portion 112. Consequently, the same effect as that of the first embodiment is provided.

Although a description is provided of the suitable embodiments of the present invention, the present invention is not limited to the same. Although in the present embodiment, a description is provided of the disposable diaper in the shape of pants having a trunk opening and a pair of leg openings by joining the front body portion and the rear body portion in predetermined adhesive portions, the present invention is not limited to the same. For example, the present invention may be applied to an unfolded-type disposable diaper that can be worn by locking a front body portion and a rear body portion using a locking member or the like.

Alternatively, the present invention may be used for a disposable diaper formed in the shape of pants, which are locked by a locking member such as a re-lockable hook-and-loop fastener, as used for an unfolded-type disposable diaper, is easily unlocked in adhesive portions in a front body portion and a rear body portion, and can be unfolded and relocked.

Furthermore, although in the present embodiment, a description is provided of a disposable diaper for adults, the present invention is not limited to the same. For example, it may be a disposable diaper for children.

EXAMPLES

A description is now provided of an experiment conducted in order to check for appropriate conditions in a coating pattern of adhesives.

1) A cut edge of a composite sheet in which a ratio of expansion and contraction of a stretchable sheet was 1.8 at the time of affixing the stretchable sheet and a non-stretchable sheet was set to 10 degrees, 30 degrees, 45 degrees, 60 degrees, and 80 degrees to an expansion and contraction direction, the width along the expansion and contraction direction of adhesive portions was a constant value of 2.5 mm, and the spacing between the adhesive portions was changed to (d) 1 mm, (e) 2.5 mm, (f) 4 mm, and (g) 7.5 mm, to examine the degree of warping occurring. For reference, the same experiment was also conducted with respect to a case (a) where adhesives were applied to the entire surface, a case (b) where the spacing between lines adjacent in a spiral shape was not more than 3 mm (a fine mesh shape), and a case (c) where the spacing between adjacent lines in a spiral shape was approximately 4 mm and was not less than 3 mm (a coarse mesh shape).

Here, the non-stretchable sheet was a 19 g/m² spunbonded sheet, and the stretchable sheet was a 35 g/m² stretchable spunbonded sheet (urethane/PP). The results are shown in Table 1, described below. Here, ○ indicates a good state, Δ indicates a slightly warped state, x indicates a significantly warped state, and xx indicates a state where the degree of warping is worse. Here, x and xx indicate that the disposable diaper is defective.

TABLE 1

| | Cut angle of end of composite sheet to expansion and contraction direction | | | | |
|---|---|---|---|---|---|
| | 10° | 30° | 45° | 60° | 80° |
| a. Coat whole surface | ○ | Δ~x | x | xx | xx |
| b. Spiral (fine mesh shape) | ○ | x | xx | xx | xx |
| c. Spiral (coarse mesh shape) | ○ | ○ | Δ | x | x |
| d. Spacing between adhesive portions; 1 mm | ○ | Δ | x | xx | xx |
| e. Spacing between adhesive portions; 2.5 mm | ○ | ○ | Δ | x | xx |
| f. Spacing between adhesive portions; 4 mm | ○ | ○ | ○ | Δ | x |

TABLE 1-continued

| | Cut angle of end of composite sheet to expansion and contraction direction | | | | |
|---|---|---|---|---|---|
| | 10° | 30° | 45° | 60° | 80° |
| g. Spacing between adhesive portions; 7.5 mm | ○ | ○ | ○ | ○ | Δ |

Table 1 shows that warping hardly occurred in a case where the adhesives were applied in a linear shape, as compared with that of a case where the adhesives were applied to the entire surface. It was found that the greater the spacing between the adhesive portions, the less warping occurred. Furthermore, it was found that even in a case where the adhesives were applied in a spiral shape continuous in a plane shape, warping did not easily occur when the spacing between the lines was coarse.

2) The results of the same experiment conducted by changing only the ratio of expansion and contraction to 1.3 in 1) are shown in Table 2.

TABLE 2

| | Cut angle of end of composite sheet to expansion and contraction direction | | | | |
|---|---|---|---|---|---|
| | 10° | 30° | 45° | 60° | 80° |
| a. Coat whole surface | ○ | Δ | x | xx | xx |
| b. Spiral (fine mesh shape) | ○ | Δ | x | xx | xx |
| c. Spiral (coarse mesh shape) | ○ | ○ | Δ | x | x |
| d. Spacing between adhesive portions; 1 mm | ○ | Δ~○ | x | xx | xx |
| e. Spacing between adhesive portions; 2.5 mm | ○ | ○ | Δ | x | xx |
| f. Spacing between adhesive portions; 4 mm | ○ | ○ | ○ | Δ | x |
| g. Spacing between adhesive portions; 7.5 mm | ○ | ○ | ○ | ○ | Δ |

Similarly to Table 1, Table 2 shows that warping hardly occurred in a case where the adhesives were applied in a linear shape, as compared with that of a case where the adhesives were applied to the entire surface. It was found that the greater the spacing between the adhesive portions, the less warping occurred. It was found that in a case where the adhesives were applied in a spiral shape continuous in a plane shape, warping did not easily occur when the spacing between the lines was large. Furthermore, it was found that the degree of warping was low until the cut angle reached 30 degrees, although the warping had already occurred when the cut angle was 30 degrees in the case where the ratio of expansion and contraction was 1.8.

3) The results of examination of the degree of occurrence of warping by setting the spacing between the adhesive portions to a constant value of 1 mm and changing the width of the adhesive portions to (a) 2.5 mm, (b) 5.0 mm, (c) 1.0 mm, and (d) 20 mm are shown in Table 3. It should be noted that no experiment was conducted with respect to cases where the width of the adhesive portions was 5.0 mm, 10 mm, and 20 mm when the cut angle was 10 degrees.

TABLE 3

| | Cut angle of end of composite sheet to expansion and contraction direction | | | | |
|---|---|---|---|---|---|
| | 10° | 30° | 45° | 60° | 80° |
| a. Width of adhesive portions; 2.5 mm | ○ | ○ | Δ | x | xx |
| b. Width of adhesive portions; 5.0 mm | — | x | x | xx | xx |
| c. Width of adhesive portions; 10 mm | — | x | xx | xx | xx |
| d. Width of adhesive portions; 20 mm | — | x | xx | xx | xx |

Table 3 shows that less warping occurred when the width of the adhesive portions was decreased.

4) The results of examination of the degree of occurrence of warping by setting the spacing between the adhesive portions to a constant value of 4 mm and changing the width of the adhesive portions to 2.5 mm, 5.0 mm, 1.0 mm, and 20 mm are shown in Table 4.

TABLE 4

| | Cut angle of end of composite sheet to expansion and contraction direction | | | | |
|---|---|---|---|---|---|
| | 10° | 30° | 45° | 60° | 80° |
| a. Width of adhesive portions; 2.5 mm | ○ | ○ | ○ | ○ | |
| b. Width of adhesive portions; 5.0 mm | ○ | ○ | Δ~○ | x | |
| c. Width of adhesive portions; 10 mm | ○ | ○ | x | xx | |
| d. Width of adhesive portions; 20 mm | ○ | ○ | xx | xx | |

Table 4 shows that less warping occurred when the width of the adhesive portions was decreased. The spacing between the adhesive portions was greater, so that the degree of warping was lower overall when compared with the results shown in Table 3.

5) The results of measurement of the degree of warping by setting the spacing between adhesive portions to a constant value of 7.5 mm and changing the width of the adhesive portions to 2.5 mm, 5.0 mm, 10 mm, and 20 mm are shown in Table 5.

TABLE 5

| | Cut angle of end of composite sheet to expansion and contraction direction | | | | |
|---|---|---|---|---|---|
| | 10° | 30° | 45° | 60° | 80° |
| a. Width of adhesive portions; 2.5 mm | ○ | ○ | ○ | ○ | Δ |
| b. Width of adhesive portions; 5.0 mm | ○ | ○ | ○ | Δ | x |
| c. Width of adhesive portions; 10 mm | ○ | ○ | Δ~○ | x | xx |
| d. Width of adhesive portions; 20 mm | ○ | ○ | x | xx | xx |

Table 5 shows that warping less easily occurred when the width of the adhesive portions was decreased. The spacing between the adhesive portions was as great as 7.5 mm, so that the degree of warping was lower overall when compared with the results shown in Table 3 and Table 4.

From the foregoing results in 1) to 5), it was found that the greater the spacing between the adhesive portions, the less warping occurred. The spacing between the adhesive portions was preferably not less than 4 mm. If the spacing was too great, however, a space was noticeable at an end of the composite sheet. Therefore, the spacing was preferably not more than 25 mm, although it varied depending on a ratio of expansion and contraction. Furthermore, it was found that the width of the adhesive portions was preferably narrow.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article having a width direction and a longitudinal direction perpendicular to the width direction, comprising:
    an absorbing member in an elongated shape disposed along the longitudinal direction of the absorbent article; and
    a chassis comprising a substantially rectangular front body member having a length extending in the width direction, a substantially rectangular rear body member having a length extending in the width direction, and an intermediate body portion arranged in the longitudinal direction between the front body member and the rear body member, said intermediate body portion having a leg-surrounding portion recessed inward in the width direction of the absorbent article on both sides in the width direction formed therein,
    wherein at least said front body member and said rear body member are each composed of a stretchable composite sheet obtained by affixing, at a plurality of adhesive portions, a first sheet having a first ratio of expansion and contraction and a second sheet having a second ratio of expansion and contraction, wherein the second sheet is more stretchable than the first sheet and is disposed on an outer side of the first sheet at an outermost surface of the front body and rear body, defining an outer surface thereof,
    wherein the plurality of adhesive portions extend in the length direction with predetermined spacing in the width direction, and
    wherein the absorbing member is adhered to the front body member and the rear body member.

2. The absorbent article according to claim 1,
    wherein the difference between the first and second ratios of expansion and contraction in the composite sheet is at least 20%.

3. The absorbent article according to claim 1,
    wherein a width of each of the plurality of adhesive portions is in the range of 0.1 mm to 20 mm.

4. The absorbent article according to claim 1,
    wherein the adhesive portions adjacent to each other at edges of the front body member and the rear body member that are adjacent the intermediate body member are spaced from one-another in the range of 4 mm to 25 mm.

5. The absorbent article according to claim 1,
    wherein a ratio of the sum of the areas of the plurality of adhesive portions, at the edges of the front and rear body members that are adjacent the intermediate body member, to a corresponding area of the composite sheet is in the range of 0.4% to 83%.

6. The absorbent article according to claim 1, wherein the absorbent article is a diaper in the shape of pants.

7. The absorbent article of claim 1, wherein the plurality of adhesive portions extend in the length direction intermittently with predetermined spacing in the width direction.

8. An absorbent article having a width direction and a longitudinal direction perpendicular to the width direction, comprising:
- an absorbing member in an elongated shape disposed along the longitudinal direction of the absorbent article; and
- a chassis comprising a substantially rectangular front body member having a length extending in the width direction, a substantially rectangular rear body member having a length extending in the width direction, and an intermediate body portion arranged in the longitudinal direction between the front body member and the rear body member, said intermediate body portion having a leg-surrounding portion recessed inward in the width direction of the absorbent article on both sides in the width direction formed therein,
- wherein at least said front body member and said rear body member are each composed of a stretchable composite sheet obtained by affixing, at a plurality of adhesive portions, a first sheet having a first ratio of expansion and contraction and a second sheet having a second ratio of expansion and contraction, wherein the second sheet is more stretchable than the first sheet and is disposed on an outer side of the first sheet at an outermost surface of the front body and rear body, defining an outer surface thereof,
- wherein the second sheet has a basis weight of 20 to 80 $g/m^2$ before affixing to the first sheet,
- wherein the plurality of adhesive portions extend in the length direction with predetermined spacing in the width direction, and
- wherein the absorbing member is adhered to the front body member and the rear body member.

* * * * *